US00PP22430P3

(12) United States Plant Patent
Bacon

(10) Patent No.: US PP22,430 P3
(45) Date of Patent: Jan. 3, 2012

(54) PLUM TREE NAMED 'SUPLUMFORTYONE'

(50) Latin Name: *Prunus salicina*
Varietal Denomination: Suplumfortyone

(75) Inventor: Terry Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 208 days.

(21) Appl. No.: 12/657,346

(22) Filed: Jan. 19, 2010

(65) Prior Publication Data

US 2011/0179534 P1 Jul. 21, 2011

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

| | | | | |
|---|---|---|---|---|
| PP8,583 | P | 2/1994 | Zaiger et al. | |
| PP13,167 | P2 | 11/2002 | Mowrey et al. | |
| PP15,888 | P2 | 7/2005 | Cain | |
| PP19,360 | P2 * | 10/2008 | Kaagman | Plt./321 |

* cited by examiner

*Primary Examiner* — Wendy C Haas
(74) *Attorney, Agent, or Firm* — Knobbe, Martens, Olson & Bear, LLP

(57) ABSTRACT

A new and distinct plum tree variety, *Prunus salicina,* cv. 'Suplumfortyone' is characterized by red flesh color.

1 Drawing Sheet

Latin name of the genus and species claimed: *Prunus salicina.*

Variety denomination: 'Suplumfortyone'.

BACKGROUND AND SUMMARY OF THE INVENTION

This invention relates to the discovery and asexual propagation of a new and distinct variety of plum, *Prunus salicina* cv. 'Suplumfortyone'. The new variety was first hybridized in 2002 and selected in 2005 by Terry Bacon as breeder number: 'PL525RB'. The new variety was first evaluated by Terry Bacon near Wasco, Calif. in Kern County. The variety 'Suplumfortyone' was originated by hybridization.

The new variety 'Suplumfortyone' is characterized by red flesh color.

The seed parent is 'Suplumtwentyfive' (the subject of U.S. Plant Pat. No. 15,888), and the pollen parent is an unknown plum in the breeding population. The parent varieties were first crossed in February of 2002, with the date of planting of the progeny being February 2003, and the date of first flowering being February 2005. The new plum variety 'Suplumfortyone' was first asexually propagated by Terry Bacon near Wasco, Kern County, Calif. in May 2005, by budding.

The new variety 'Suplumfortyone' is distinguished from its seed parent, 'Suplumtwentyfive', in that the new variety has red flesh color while 'Suplumtwentyfive' has amber flesh color.

The new variety 'Suplumfortyone' has a similar ripening time as 'Earliqueen' (U.S. Plant Pat. No. 8,583), but the new variety has red flesh color while 'Earliqueen' has amber flesh color. The new variety 'Suplumfortyone' also has a similar ripening time as 'Suplumtwentythree' (U.S. Plant Patent No. 13,167), but the new variety reaches full bloom at about February 12$^{th}$, while 'Suplumtwentythree' reaches full bloom at about March 1$^{st}$.

The new variety 'Suplumfortyone' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new plum variety 'Suplumfortyone'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The descriptive matter which follows pertains to 4 year old 'Suplumfortyone' plants on Nemared (unpatented) rootstock, grown in the vicinity of Wasco, Kern County, Calif., during 2009, and is believed to apply to plants of the variety grown under similar conditions of soil and climate elsewhere.

TREE

General: (Measurements taken on 4 year old tree unless otherwise noted.)

*Size.*—Medium. Normal for most plum varieties. Reaches a height of approximately 3 meters with normal pruning.

*Spread.*—Normal for most plum varieties. Approximately 3 meters.
*Vigor.*—Moderately vigorous.
*Growth.*—Spreading.
*Productivity.*—Productive.
*Form.*—Vase formed.
*Bearer.*—Regular.
*Fertility.*—Requires pollination to set a full crop.
*Canopy density.*—Medium-dense.
*Hardiness.*—Hardy in all fruit growing areas of California. Winter chilling requirement is approximately 250 hours at or below 7.2° C.
*Disease resistance/susceptibility.*—No specific testing for relative plant disease resistance/susceptibility has been undertaken. Under close observation in, Kern County, Calif., no particular plant/fruit disease resistance/susceptibility has been observed.

Trunk: (Measurements at approximately 30 cm above soil line.)
*Diameter.*—Approximately 14 cm, varies with soil type, fertility, climatic conditions and cultural practices.
*Texture.*—Medium shaggy, increases with age of tree.
*Trunk color.*—About Medium Grey 201B to Light Greyed-orange 174C; becomes darker with age.

Branches: (Measurements at approximately 90 cm above soil line.)
*Size.*—Diameter approximately 6 cm.
*Texture.*—Medium, Shaggy.
*Color.*—Varying between from Medium Grey 201A to Light Greyed-orange 174C; becomes darker with age.
*Number of lenticels.*—Numerous.
*Lenticels density.*—Approximately 2-4 per $cm^2$.
*Lenticels color.*—About Medium Greyed-orange 174B.
*Lenticels size.*—Medium; approximately 1 mm by 5 mm.
*Lenticels length.*—Approximately 3 mm.
*Lenticels width.*—Approximately 1 mm.

Flowering shoots: (Data taken in July at midpoint of previous season shoots.)
*Size.*—Average diameter approximately 6 mm.
*Color.*—Topside: About Dark Greyed-orange 165B. Underside: About Dark Greyed-orange 165B.
*Internode length.*—Medium; approximately 1-3 cm. Midway on flowering shoot.
*Flowering shoot lenticels.*—Plentiful. Color: About Dark Greyed-green 197B. Diameter: Approximately 0.7 mm.
*Flowering shoot leaf buds.*—Shape: Conical. Width: Approximately 1 mm. Length: Approximately 2 mm. Color: About Dark Greyed-orange 177A.
*Flowering shoot flower buds.*—Shape: Conical. Width: Approximately 1.5 mm. Length: Approximately 3 mm. Color: About Dark Greyed-orange 177A. Number of buds per node: Usually 2-3.
*Density of buds.*—Medium.
*Flower bud distribution.*—Generally on spurs and one year old shoots and older wood.
*Ratio of wood (leaf) buds to flowering shoots.*—1/2.

FOLIAGE

Leaves:
*Size.*—Medium.
*Average length.*—Medium; approximately 70-100 mm without petiole.
*Average width.*—Medium; approximately 35-50 mm.
*Thickness.*—Medium.
*Color.*—Upper surface: About Dark Green 137C. Lower surface: About Light Yellow-green 147C.
*Form.*—Broad, Obovate.
*Tip.*—Cuspidate.
*Base.*—V-shaped.
*Margin.*—Crenate.
*Venation.*—Pinately veined.
*Vein color.*—About Light Green 139D.
*Surface texture.*—Smooth.
*Leaf blade (ratio of length to width).*—Medium; about 2/1.
*Shape in the cross section.*—Concave.
*Profile.*—Up folded.
*Leaf blade tip.*—Curved downwardly.
*Undulation of margin.*—Slight.

Petiole:
*Average length.*—Medium; approximately 12-15 mm.
*Average diameter.*—Approximately 2 mm.
*Color.*—About Light Green 139D.
*Thickness.*—Medium; approximately 2 mm.

Stipules:
*Number/leaf bud.*—Approximately 2.
*Typical length.*—Approximately 7 mm.
*Color.*—About Medium Greyed-brown 199B when dry.
*Persistence.*—Falls off.

Leaf glands:
*Form.*—Globose-Reniform mixed.
*Average number.*—Usually 2-4.
*Position.*—On both leaf base and petiole; opposite.
*Average size.*—Medium; approximately 0.9 mm.
*Color.*—About Dark Greyed-orange 166B.

FLOWERS

General:
*Flower blooming period.*—First bloom: Approximately Feb. 5, 2009. Full bloom: Approximately Feb. 12, 2009.
*Time of bloom.*—Early.
*Duration of bloom.*—Long; approximately 18 days.
*Diameter of fully opened flower.*—Medium, approximately 18 mm.
*Flower aroma.*—Slight aroma.
*Shape.*—Rosaceous.

Peduncle:
*Length.*—Medium; approximately 7 mm.
*Diameter.*—Slender; approximately 1.7 mm.
*Color.*—About Yellow-green 144B.
*Pubescence.*—Absent.

Petals:
*Number.*—5.
*Arrangement.*—Overlapping slightly.
*Length.*—Approximately 8 mm.
*Diameter.*—Approximately 6 mm.
*Shape.*—Broad elliptic.
*Apex shape.*—Rounded.
*Base shape.*—Narrows at point of attachment.
*Color.*—white.
*Surface texture.*—Smooth.
*Margins.*—Slightly undulating; entire.
*Claw length.*—Medium.
*Margin waviness.*—Medium.
*Base angle.*—Narrow.
*Division of upper margin.*—Entire.
*Pubescence of inner surface.*—Absent.
*Pubescence of outer surface.*—Absent.

Sepals:
*Number.*—5.
*Length.*—Approximately 6 mm.
*Diameter.*—Approximately 4 mm.
*Shape.*—Triangular.

*Color.*—About Yellow-green 144A.
*Surface texture.*—Smooth.
*Margins.*—Entire.
*Positioning.*—Adpressed to petals.
*Pubescence of inner surface.*—Absent.
*Pubescence of outer surface.*—Absent.

Stamens:
*Number.*—Ranges from approximately 20 to approximately 30.
*Average length.*—Approximately 5-15 mm.
*Filament color.*—About white.
*Anther color.*—About Medium Greyed-yellow 162A.
*Flower pollen color.*—About Medium Greyed-yellow 162A when dried.
*Position.*—Perigynous.

Pistil:
*Number.*—Usually one, occasionally two.
*Average length.*—Approximately 8-10 mm.
*Ovary diameter.*—Approximately 1 mm.
*Pubescence.*—None.
*Stigma extension in comparison to anthers.*—Usually below.
*Frequency of supplementary pistils.*—Few.

Receptacle:
*Depth.*—Medium.
*Pubescence of inner surface.*—Absent.
*Pubescence of outer surface.*—Absent.

FRUIT

General: (Description taken near Wasco, Kern County, Calif.)
*Harvest.*—Date of first pick: Approximately May 21. 2009. Date of last pick: Approximately May 30, 2009.
Maturity when described: Firm-mature.
Season ripening: Early.
Position of maximum diameter: Towards the middle.
Symmetry about the suture: Symmetric.

Size:
*Length* (*stem end to apex*).—Approximately 50 mm.
*Diameter in line with suture plane.*—Approximately 50 mm.
*Diameter perpendicular to suture plane.*—Approximately 60 mm.
*Average weight.*—Approximately 115 gm.

Form:
*Viewed from apex.*—Rounded, nearly symmetrical.
*Viewed from side, facing suture.*—Rounded, nearly symmetrical.
*Viewed from side, perpendicular to suture.*—Rounded, nearly symmetrical.

Apex shape: Rounded with slightly indented tip.
Apex base: Rounded.

Fruit stem cavity:
*Shape.*—Rounded.
*Depth.*—Medium; Approximately 0.5 cm.
*Breadth.*—Approximately 2-3 cm.
*Width.*—Medium; Approximately 2-3 cm.

Fruit stem:
*Length.*—Medium; Glabrous; Approximately 9 mm.
*Diameter.*—Approximately 3 mm.
*Color.*—About Light Yellow-green 147D.
*Adherence to stone.*—Medium.

Fruit skin:
*Thickness.*—Medium.
*Adherence to flesh.*—Very strong.
*Surface texture.*—Smooth-Medium.
*Pubescence.*—None.
*Bloom.*—Medium.
*Ground color.*—About Dark Red 46A, when visible.
*Overcolor.*—About Dark Greyed-purple 187A to Black 202A.
*Taste.*—Mildly tart.
*Reticulation.*—Absent.
*Roughness.*—Absent.
*Tendency to crack.*—None in wet season.
*Tenacity.*—Tenacious to flesh.

Flesh:
*Ripens.*—Evenly.
*Texture.*—Fine.
*Fibers.*—Few.
*Flavor.*—Mildly-sweet.
*Brix.*—Approximately 15°.
*Juice.*—Moderate.
*Aroma.*—Slight.
*Color.*—About Medium Red 46B.
*Acidity.*—Medium-low.
*Eating quality.*—Good.
*Stone/flesh ratio.*—1/50.
*Firmness.*—Medium.

Pit cavity size:
*Length* (*diameter in line with suture plane*).—Approximately 20 mm.
*Diameter in line with suture plane.*—Approximately 20 mm.
*Diameter perpendicular to suture plane.*—Approximately 10 mm.
*Color.*—About Medium Red 46B.

Fruit use: Fresh market.
Fruit shipping and keeping quality: Good, holds well in cold storage and maintains good firmness and eating quality, minimal bruising and scarring in packing and shipping trials.

Stone: (Measurements taken on dried stones.)
*Stone freeness.*—Cling.
*Degree of adherence to flesh.*—Medium.
*Stone size.*—Size compared to Fruit: Medium. Length (Diameter in line with suture plane): Approximately 20 mm. Diameter in Line with Suture Plane: Approximately 20 mm. Diameter perpendicular to suture plane: Approximately 10 mm. Width of Stalk End: Medium; approximately 3 mm. Angle of Stalk end: Right angle. Hilum: Oval.
*Stone form.*—Viewed from side: Nearly oval; somewhat irregular. Viewed from ventral side: Somewhat oval-flattened. Viewed from stem end: Oval, nearly symmetrical.
*Stone shape.*—Base shape: Nearly straight. Apex shape: Rounded with small point.
*Stone surface.*—Furrowed and pitted irregularly throughout.
*Stone halves.*—Nearly equal.
*Stone ridges.*—Rounded and continuous.
*Stone outgrowing keel.*—Partially developed.
*Stone tendency to split.*—Slight in wet season.
*Stone color.*—About Medium Greyed-orange 163B when dried.
*Position of maximum.*—Toward middle.
*Ventrical edge.*—Thin with slight wing toward middle.
*Dorsal edge.*—Narrow, continuous.

What is claimed is:

1. A new and distinct plum tree as herein described and illustrated.

* * * * *

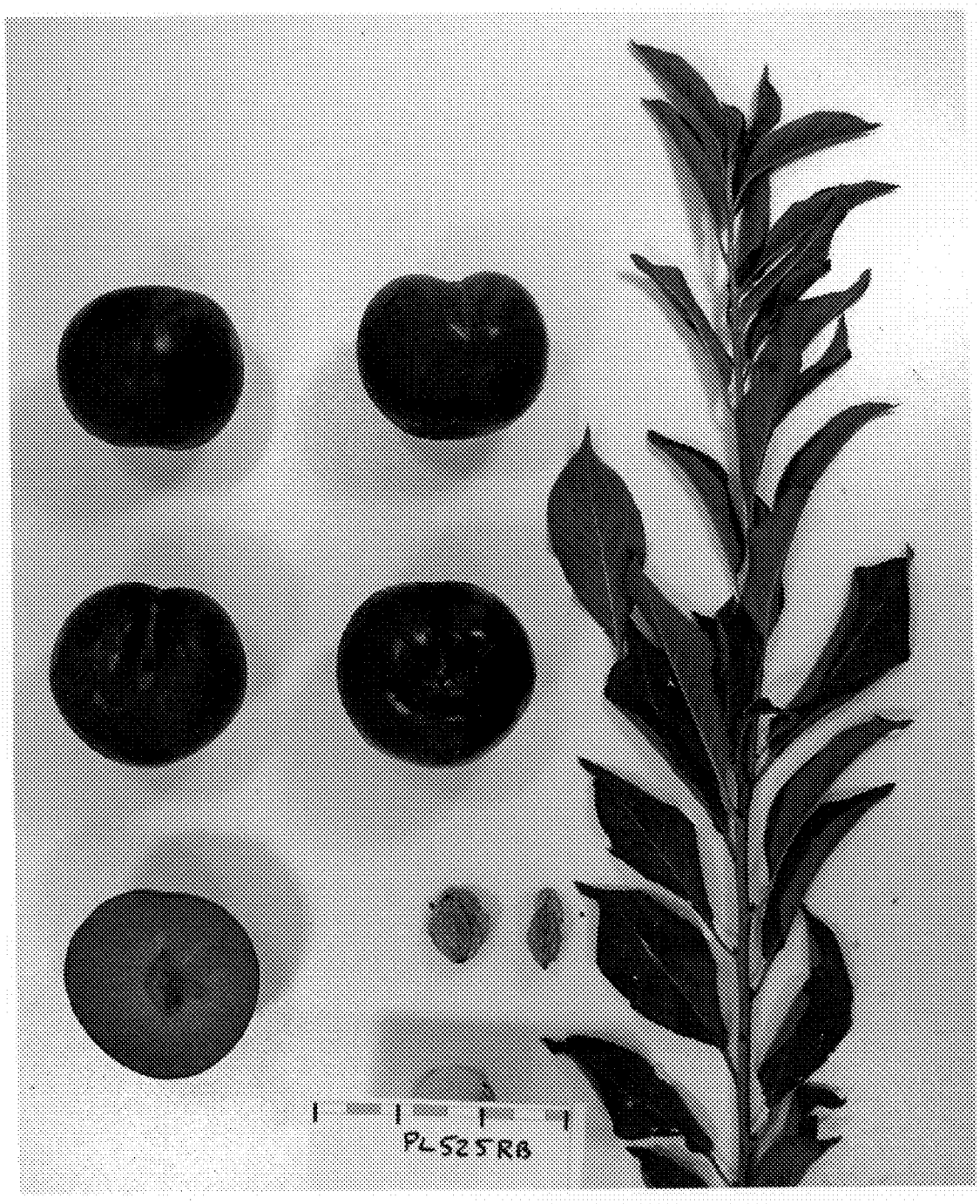
PL525RB